United States Patent
Nelson

(10) Patent No.: US 12,251,400 B2
(45) Date of Patent: Mar. 18, 2025

(54) LIQUID CONCENTRATES OF CALCIUM AND MAGNESIUM

(71) Applicant: BIOLINK LIFE SCIENCES, INC., Cary, NC (US)

(72) Inventor: Deanna J. Nelson, Cary, NC (US)

(73) Assignee: BIOLINK LIFE SCIENCES, INC., Cary, NC (US)

( * ) Notice: Subject to any disclaimer, the term of this patent is extended or adjusted under 35 U.S.C. 154(b) by 726 days.

(21) Appl. No.: 17/603,072

(22) PCT Filed: Apr. 10, 2020

(86) PCT No.: PCT/US2020/027644
§ 371 (c)(1),
(2) Date: Oct. 12, 2021

(87) PCT Pub. No.: WO2020/210608
PCT Pub. Date: Oct. 15, 2020

(65) Prior Publication Data
US 2022/0175828 A1     Jun. 9, 2022

Related U.S. Application Data

(60) Provisional application No. 62/833,094, filed on Apr. 12, 2019.

(51) Int. Cl.
| | |
|---|---|
| *A61K 33/06* | (2006.01) |
| *A61K 9/08* | (2006.01) |
| *A61K 31/122* | (2006.01) |
| *A61K 31/593* | (2006.01) |
| *A61P 3/12* | (2006.01) |

(52) U.S. Cl.
CPC ............... *A61K 33/06* (2013.01); *A61K 9/08* (2013.01); *A61K 31/122* (2013.01); *A61K 31/593* (2013.01); *A61P 3/12* (2018.01)

(58) Field of Classification Search
None
See application file for complete search history.

(56) References Cited

U.S. PATENT DOCUMENTS

| | | | | |
|---|---|---|---|---|
| 5,324,442 | A * | 6/1994 | Mathews | C09K 3/185 252/70 |
| 8,247,000 | B2 * | 8/2012 | Lewis | A61P 7/00 424/682 |
| 8,591,938 | B2 | 11/2013 | Tarallo | |
| 8,592,480 | B2 | 11/2013 | Tarallo | |
| 9,089,528 | B2 | 7/2015 | Tarallo | |
| 2010/0009948 | A1 | 1/2010 | Nelson et al. | |
| 2018/0193312 | A1 | 7/2018 | Swanson et al. | |

FOREIGN PATENT DOCUMENTS

WO    WO 2008/116215    9/2008

OTHER PUBLICATIONS

International Search Report and Written Opinion for PCT/US20/27644. Mailed Jun. 30, 2020. 17 pages.
Calcium Propionate. USDA. 2002. Retrieved from the internet 2022. 19 pages.
Chui et al., Pill burden, adherence, hyperphosphatemia, and quality of life in maintenance dialysis patients. Clin J Am Soc Nephrol. Jun. 2009;4(6):1089-96.
Ciarlo et al., Impact of the microbial derived short chain fatty acid propionate on host susceptibility to bacterial and fungal infections in vivo. Sci Rep. Nov. 29, 2016;6:37944.
De Francisco et al., Evaluation of calcium acetate/magnesium carbonate as a phosphate binder compared with sevelamer hydrochloride in haemodialysis patients: a controlled randomized study (CALMAG study) assessing efficacy and tolerability. Nephrol Dial Transplant. Nov. 2010;25(11):3707-17.
De Schutter et al., Effect of a magnesium-based phosphate binder on medial calcification in a rat model of uremia. Kidney Int. Jun. 2013;83(6):1109-17.
Gold et al., Gastric acid secretion and serum gastrin levels in patients with chronic renal failure on regular hemodialysis. Nephron. 1980;25(2):92-5.
Hardy et al., Inhibition of gastric secretion by omeprazole and efficiency of calcium carbonate on the control of hyperphosphatemia in patients on chronic hemodialysis. Artif Organs. Jul. 1998;22(7):569-73.
Helal et al., Efficacy and safety of calcium acetate-magnesium carbonate in the treatment of hyperphosphatemia in dialysis patients. Saudi J Kidney Dis Transpl. Nov.-Dec. 2016;27(6):1162-1167.
Hutchison et al., Use of magnesium as a drug in chronic kidney disease. Clin Kidney J. Feb. 2012;5(Suppl 1):i62-i70.
Meric et al., Etiology of hypercalcemia in hemodialysis patients on calcium carbonate therapy. Am J Kidney Dis. Nov. 1990;16(5):459-64.
Neven et al., A magnesium based phosphate binder reduces vascular calcification without affecting bone in chronic renal failure rats. PLoS One. Sep. 17, 2014;9(9):e107067. 9 pages.
Parsons et al., Successful control of hyperparathyroidism in patients on continuous ambulatory peritoneal dialysis using magnesium carbonate and calcium carbonate as phosphate binders. Nephron. 1993;63(4):379-83.
Tan et al., Ranitidine reduces phosphate binding in dialysis patients receiving calcium carbonate. Nephrol Dial Transplant. May 1996;11(5):851-3.

(Continued)

*Primary Examiner* — Alton N Pryor
(74) *Attorney, Agent, or Firm* — Casimir Jones, S.C.; J. Mitchell Jones

(57) ABSTRACT

The present invention relates to a liquid concentrate of calcium propionate and a magnesium salt, optionally with sweetener, taste-masking agent, flavoring, and thickening agent. Also provided is a method for binding phosphorus in ingesta, and inhibiting absorption of phosphorus from the gastrointestinal tract of a subject by administering to the subject a liquid concentrate of at least calcium salt and magnesium salt.

20 Claims, No Drawings

(56) References Cited

OTHER PUBLICATIONS

Tonelli et al., Oral phosphate binders in patients with kidney failure. N Engl J Med. Apr. 8, 2010;362(14):1312-24.

* cited by examiner

LIQUID CONCENTRATES OF CALCIUM AND MAGNESIUM

CROSS REFERENCE TO RELATED APPLICATIONS

This application is a U.S. 371 national phase entry of International Patent Application No. PCT/US2020/027644, filed Apr. 10, 2020, which claims priority to and the benefit of U.S. Provisional Application No. 62/833,094, filed Apr. 12, 2019, which are hereby incorporated by reference in their entireties.

FIELD OF THE INVENTION

The present invention relates to aqueous liquid concentrates of calcium propionate, a magnesium salt, and vitamins $D_3$ and $K_2$, optionally with sweetener, taste-masking agent, flavoring, and thickening agent. Also provided is a method for binding phosphorus in ingesta, and inhibiting absorption of phosphorus from the gastrointestinal tract of a subject by administering to the subject a liquid concentrate of calcium propionate, magnesium salt, and vitamins $D_3$ and $K_2$.

BACKGROUND OF THE INVENTION

In subjects with chronic kidney disease (CKD), phosphorus retention (as evidenced by abnormally elevated serum phosphorus levels) may contribute to progression of renal failure and is a major factor in the development of secondary hyperparathyroidism, renal osteodystrophy, and soft tissue calcification. [Tonelli M, Pannu N, Manns B. Oral phosphate binders in patients with kidney failure. New England J Med 2010; 362: 1312-1324.] Hyperphosphatemia in CKD patients is treated by restriction of phosphorus in the diet and pharmacological means. Serum phosphorus is also reduced during dialysis of end-stage renal disease patients undergoing such treatment.

Methods for the prevention and treatment of hyperphosphatemia include the use of compounds or compositions that will bind phosphorus in the gastrointestinal (GI) tract of a subject and prevent its absorption into the systemic circulation. Compounds that bind phosphorus in the GI tract are known as phosphorus binders. Phosphorus binding is a chemical reaction between dietary phosphorus-containing anions and a cation of a binder compound. Chemical reaction results in the formation of insoluble and hence unabsorbable phosphate compounds, adsorption of phosphorus-containing anions on the surface of binder particles, or a combination of both processes. Today, oral phosphorus binders are used in over 90% of patients with kidney failure.

Subjects having renal failure have a high burden of co-existing diseases, poor health-related quality of life, and are prescribed many medications. Chiu et al. reported that the median daily "pill burden" (i.e., solid oral dosages of medications) of these patients was 19; in one-quarter of these subjects, it exceeded 25 pills per day. [Chui Y W, et al., Clin J Am Soc Nephrol 2009; 4: 1089-1096.] Phosphorus binders accounted for about one-half of the daily pill burden; 62% of the participants in the Chiu study were non-adherent to phosphate binder dosage regimens, with the greatest non-adherence exhibited in patients prescribed 12 or more phosphorus binder pills per day. Higher pill burden was also independently associated with lower quality of life.

Clinicians have concluded that reducing pill burden may improve patient adherence and quality of life in patients such as those described above. There are two components to the pill burden: (1) the number of tablets to be taken at a given time and (2) the frequency of administration. Hypothetically, therefore, pill burden could be reduced by (a) reducing the number of pills taken at each dosing interval; or (b) reducing the frequency of administration. Neither strategy can be used with any of the currently available phosphorous binder pills. Thus, the number of tablets to be taken at a given time cannot be reduced, since combining two or three smaller pills into a single tablet provides a large dosage form that is difficult to swallow. Likewise, reducing the frequency of administration by administering single daily dosages has proven inferior to doses administered thrice daily (i.e., with every meal).

The only conventional solution to the pill burden problem is a liquid formulation of calcium acetate, as described in U.S. Pat. Nos. 8,591,938, 8,592,480, and 9,089,528. Calcium acetate is potently repugnant to the palate. Therefore, this solution provides calcium acetate in a sweetened formulation containing taste-masking agents, flavoring agents, and preservatives to improve tolerability. However, this solution fails to address the increased risks of hypercalcemia and vascular calcification associated with calcium acetate phosphate binders. Consequently, there is a long-standing and heretofore unmet need for a liquid composition that achieves effective phosphorus binding without increased risk of hypercalcemia and vascular calcification.

SUMMARY OF THE INVENTION

The invention satisfies this unmet need and others by providing, in one embodiment, a liquid concentrate comprising a solution of calcium propionate, a water-soluble magnesium salt, and vitamins $D_3$ and $K_2$, wherein the combination of salts dissolves completely in water. In other embodiments, the liquid concentrate comprises an aqueous solution comprising about 2-5 mmol calcium propionate and about 1-5 mmol magnesium salt per 5 milliliters of solution, where the magnesium salt is magnesium propionate, magnesium lactate, magnesium L-lactate, magnesium threonate, magnesium butyrate, or magnesium L-theanate.

In one embodiment, five mL of the inventive composition provides 110 milligrams (mg) of calcium as calcium propionate and 60 mg of magnesium as magnesium propionate, magnesium lactate, magnesium L-lactate, magnesium L-theanate, magnesium butyrate or magnesium L-threonate.

In other embodiments, the liquid concentrate comprises calcium magnesium propionate, wherein said propionate provides 110 milligrams of calcium and 60 milligrams of magnesium in each 5 mL of said concentrate. In other embodiments, the liquid concentrate comprises calcium magnesium propionate, wherein said calcium magnesium propionate provides 220 mg of calcium and 60 mg of magnesium in each 5 mL of said concentrate.

In other embodiments, the liquid concentrate also comprises a sweetener, a taste-masking agent, a flavoring agent, a coloring agent, and/or a thickening agent.

In other embodiments, the liquid concentrate does not contain one or more of the following ingredients: calcium acetate (anhydrous or hydrous); calcium carbonate; magnesium acetate (anhydrous or hydrous); magnesium oxide; magnesium ascorbate; magnesium glycinate; magnesium bis(glycinate); or magnesium carbonate.

The present invention also provides, in another embodiment, a method for binding phosphorus within the gastrointestinal tract of an individual, comprising administering to the subject a liquid concentrate of calcium propionate, a magnesium salt, and vitamins $D_3$ and $K_2$, as described above. In this regard, the present invention will be useful in treating subjects suffering from one or more of the following disorders: hyperphosphatemia, renal disease, kidney disease, end stage renal disease, and chronic kidney disease.

The present invention also provides, in yet another embodiment, a method for reducing the pill burden of patients exhibiting hyperphosphatemia, comprising administering to the subject a liquid concentrate of calcium propionate, a magnesium salt, and vitamins $D_3$ and $K_2$, as described above. In this regard, the present invention will be useful in treating subjects suffering from one or more of the following disorders: hyperphosphatemia, renal disease, kidney disease, end stage renal disease, and chronic kidney disease.

Administration of the liquid concentrate of the present invention according to the method described herein is associated with enhanced patient compliance and fewer adverse effects than is evident in administering presently available phosphorus binding medications. This improved patient compliance with a phosphate-binding agent is expected to improve management of the disease process.

Administration of the liquid concentrate of the present invention according to the method described herein also provides, for the first time, a palatable phosphate-binding formulation that is easily apportioned into doses suitable for infants and children and is easily administered to infants, children, and subjects having difficulty in swallowing solid dosage forms (i.e., those with dysphagia).

In further preferred embodiments, the present invention provides methods for binding phosphorus within the gastrointestinal tract of a subject, comprising orally administering to said subject a liquid concentrate comprising: an aqueous solution of calcium propionate and a magnesium salt in a molar ratio of from 1.5:1 to 1:1.5, wherein the calcium propionate concentration in said aqueous solution is from 0.175 to 0.375 molar, the magnesium salt concentration in said aqueous solution is from 0.15 to 0.35 molar, the pH of said aqueous solution is in the range from pH 5 to pH 7.5, and said magnesium salt is selected from the group consisting of magnesium lactate, magnesium L-lactate, magnesium propionate, magnesium threonate, magnesium butyrate, and magnesium theanate. In some embodiments, the molar ratio of calcium propionate:magnesium salt is from 1.3:1 to 1:1.3. In some embodiments, the molar ratio of calcium propionate:magnesium salt is about 1.1:1. In some embodiments, the aqueous solution contains about 24 milligrams calcium and 12 milligrams magnesium per milliliter of said aqueous solution. In some embodiments, the aqueous solution contains 6-10 micrograms of vitamin K2 and 40-80 International Units of vitamin D3 per milliliter of said aqueous solution.

In still further preferred embodiments, the present invention provides methods for providing calcium and magnesium as a liquid concentrate, comprising dissolving calcium propionate and magnesium propionate in water to provide an aqueous solution wherein the calcium propionate concentration in said aqueous solution is from 0.175 to 0.375 molar and the magnesium propionate concentration in said aqueous solution is from 0.15 to 0.35 molar, the molar ratio of calcium propionate:magnesium propionate of from 1.5:1 to 1:1.5, and adjusting the pH of the resulting concentrate into the range from pH 5 to pH 7.5. In some embodiments, the methods further comprise adding about 6-10 micrograms of vitamin K2 and 40-80 International Units of vitamin D3 per milliliter to said aqueous solution.

In still further preferred embodiments, the present invention provides an aqueous solution for oral administration comprising calcium magnesium propionate, wherein the calcium magnesium propionate concentration in the said solution is from 0.175 to 0.375 molar, the pH of said solution is from pH 5 to pH 7.5, and the molar ratio of calcium to magnesium in said salt is in the range from 1:2 to 2:1. In some embodiments, the molar ratio of calcium:magnesium in said salt is from 1.3:1 to 1:1.3. In some embodiments, the molar ratio of calcium propionate:magnesium in said salt is about 1.1:1. In some embodiments, the aqueous solution contains about 24 milligrams calcium and 12 milligrams magnesium per milliliter of said aqueous solution. In some embodiments, the aqueous solution contains 6-10 micrograms of vitamin K2 and 40-80 International Units of vitamin D3 per milliliter of said aqueous solution.

In still further preferred embodiments, the present invention provides methods for reducing the pill burden of a hyperphosphatemic subject, comprising orally administering to said subject a liquid concentrate comprising an aqueous solution of from about 1.5 to 3.5 mmol calcium magnesium propionate in each 5 mL of said aqueous solution, said aqueous solution having a pH of from 5 to 7.5. In some embodiments, the aqueous solution contains about 20 to 50 milligrams calcium and 10 to 25 milligrams magnesium per milliliter of said aqueous solution. In some embodiments, the aqueous solution contains 6-10 micrograms of vitamin K2 and 40-80 International Units of vitamin D3 per milliliter of said aqueous solution.

In still further preferred embodiments, the present invention provides methods for providing calcium and magnesium as a liquid concentrate, comprising dissolving calcium magnesium propionate in water to provide an aqueous solution comprising from 0.15 to 0.35 molar calcium magnesium propionate and adjusting the pH of the resulting concentrate into the range from pH 5 to pH 7.5. In some embodiments, the methods further comprise adding about 6-10 micrograms of vitamin K2 and 40-80 International Units of vitamin D3 per milliliter to said aqueous solution.

In still other embodiments, the present invention provides an aqueous solution for oral administration comprising 1.5 to 3.5 mmol calcium magnesium propionate in each 5 mL of said aqueous solution, said aqueous solution having a pH of from 5 to 7.5. In some embodiments, the aqueous solution contains about 20 to 50 milligrams calcium and 10 to 25 milligrams magnesium per milliliter of said aqueous solution. In some embodiments, the aqueous solution contains 6-10 micrograms of vitamin K2 and 40-80 International Units of vitamin D3 per milliliter of said aqueous solution.

In some preferred embodiments, the present invention provides for use of an aqueous solution as described above for binding phosphorus within the gastrointestinal tract of a subject. In some embodiments, the subject has hyperphosphatemia. In some embodiments, the subject has chronic kidney disease.

DETAILED DESCRIPTION OF THE INVENTION

The present invention stems from the surprising discovery that calcium propionate can be formulated with a water-soluble magnesium salt in a very small volume of water to provide a liquid concentrate that is tasteful to the palate. The liquid concentrate thus obtained possesses a number of advantages over solid formulations of phosphorus binders and overcomes limitations that would otherwise be encountered in administration of calcium acetate in liquid form. Further, the liquid concentrate can be formulated with vitamins $D_3$ and $K_2$ in amounts sufficient to induce beneficial enzymes having activities that reduce the risk of and slow the rate of progression of ectopic calcification, a factor correlated with reduced glomerular filtration rate and mortality in chronic kidney disease patients.

The present invention further provides a method of treating hyperphosphatemia by administering to a subject in need of treatment any one of the novel compositions described herein. Said methods prevent phosphate absorption from the gastrointestinal tract in a warm-blooded animal, thereby reducing serum phosphorus levels in the animal, and concomitantly reduces the risk of adverse effects associated with calcium acetate-containing phosphate binders. Utility of methods of the present invention has been confirmed by demonstrations of effective phosphate-binding without the generation of volatile acids, distasteful acids, and flatulence, or other side effects of conventional phosphate binder preparations.

Moreover, the present invention also provides a method for reducing the pill burden of patients exhibiting hyperphosphatemia, comprising administering to the subject a liquid concentrate of calcium propionate, a magnesium salt, and vitamins $D_3$ and $K_2$.

The term "phosphorus," in defining use of a phosphate-binder composition of the present invention, is intended to embrace both inorganic and organic anions of phosphorus in the various forms that are capable of electrostatic reaction with calcium and magnesium, including, by way of example, phosphate ($H_2PO_4^{1-}$, $HPO_4^{2-}$, and $PO_4^{3-}$), pyrophosphate ($P_2O_7^{4-}$), and the like.

The terms "calcium (Ca)" and "magnesium (Mg)" mean the calcium ion, $Ca^{2+}$ and the magnesium ion, $Mg^{2+}$, respectively.

A "pill" is a solid dosage form, such as a tablet, capsule, sprinkle, microsphere, nanosphere, and so forth.

For the purposes of this disclosure, the term "liquid concentrate" includes solutions having low viscosity (e.g., having a viscosity similar to that of water) as well as semi-solid preparations having greatly increased viscosity but retaining the property of flow (e.g., thickened aqueous liquids).

The phrase "therapeutically effective" is intended to qualify the amounts of calcium and magnesium for use in the orally administered therapy which will achieve the goal of reducing elevated serum phosphorus levels by reducing or inhibiting, for example, the absorption of phosphorus from ingesta in the gastrointestinal tract, while avoiding adverse side effects typically associated with calcium-containing phosphorus binding agents.

For the purpose of this disclosure, a warm-blooded animal is a member of the animal kingdom which includes but is not limited to mammals and birds. The most preferred mammal of this invention is human.

The inventor has discovered a liquid concentrate composition comprising a concentrated aqueous solution comprising calcium propionate and a water-soluble magnesium salt that provides unexpectedly effective phosphorus binding action and does not cause the side effects characteristic of conventional calcium-containing phosphate binders. The liquid composition offers numerous advantages as compared to conventional phosphate binders, including those advantages described in greater detail below.

First, the liquid composition obviates the need for patients to consume large numbers of pills containing conventional phosphate binders. In this regard, clinicians and patients believe that compliance with dosage regimens will be enhanced, leading to improved disease management and quality of life.

Second, the composition of this invention contains both calcium ion and magnesium ion. Both calcium and magnesium are phosphate-binding agents. In the presence of magnesium, calcium uptake from the gastrointestinal tract is reduced. As a result, the risk of adverse effects related to levels of calcium in excess of normal serum values is reduced. Magnesium is a required physiological ion that is frequently deficient, and the composition provides magnesium supplementary to dietary magnesium. Compositions comprising calcium and magnesium exhibit an efficiency of phosphate binding that is comparable to that of sevelamer carbonate, a standard of care. Users experience and appreciate improved motility afforded by the addition of magnesium and the reduction of calcium as compared to conventional phosphorus binders. The compositions also contain vitamins $D_3$ and $K_2$ in amounts known to be sufficient to elicit expression of enzymes such as osteocalcin and carboxylated osteocalcin exhibiting full activity, further reducing the risk of adverse cardiovascular events.

Third, the composition of this invention can be formulated in very small volumes. Therefore, it contributes only a negligible amount of fluid to a subject's daily fluid intake. This attribute is important for children and the elderly, who object to imbibing large volumes of liquid, as well as patients on dialysis who must regulate their daily fluid intake.

Fourth, patients no longer have to swallow multiple phosphate binder pills together before each meal. Typically, the inventive composition can be ingested orally just before, during, or shortly after each meal. Not having to swallow multiple phosphate binder pills before each meal makes the overall treatment regimen a more pleasant experience, thereby ensuring high levels of patient compliance.

Fifth, the inventive composition is palatable, i.e., has a good taste. This attribute makes the treatment regimen a more pleasant experience, thereby enhancing patient compliance.

Sixth, the inventive composition can be formulated to have low calorie content and/or a low glycemic index compared with liquid pharmaceutical formulations that are made using traditional sweeteners such as glucose or fructose. The inventive composition is inherently sweet. However, some subjects may require the addition of sweetening agents or taste-masking agents to improve palatability. If this is the case, conventional non-caloric or low caloric sweeteners or taste-masking agents may be added.

Seventh, the inventive composition is inhibitory to growth of micro-organisms. Calcium propionate is widely used as a food preservative (i.e., an inhibitor of the growth of micro-organisms and mold). [See, by way of example, ams.usda-.gov/sites/default/files/media/Calcium%20Propionate%20TR.pdf.] Although magnesium salts are not known to exhibit similar inhibitory effects on the growth of micro-organisms, the propionate anion, a physiological short-chain fatty acid, is known to exert beneficial effects on the immune system and human health without increasing the risk of developing infections. [See, Ciarlo E, et al. Sci Rep. Nov. 29, 2016; 6: 37944. doi: 10.1038/srep379441.]

Eighth, the inventive composition counteracts hypoglycemic and hyperketonemic effects of triglycerides. Magnesium propionate induces gluconeogenesis and reduces ketosis in subjects having high serum triglycerides, a frequent clinical observation in subjects who are diabetic and exhibiting compromised renal function.

Ninth, the inventive composition can be formulated to enable easy adjustment of the dose. This attribute allows the clinician or patient to adjust the dose to better prevent or treat hyperphosphatemia in both adults and children. In contrast, breaking or crushing pills increases the risk that an inappropriate dose of phosphate binder may be administered, potentially increasing the risk of adverse events.

Compositions of the invention are administered in a pharmaceutically acceptable oral liquid dosage form. In some embodiments, inventive compositions are formulated as an oral liquid nutritional supplement. In a most preferable embodiment of the present invention, a dose of the oral liquid concentrate is ingested close in time with food and/or beverage consumption (i.e., concurrent with and/or within about 1 hour before or after ingestion of food or beverages).

Solid forms of magnesium carbonate, magnesium hydrogen carbonate, magnesium oxide, and magnesium hydroxide have been used for many years, alone or in combination with other metal salts, as drugs for the treatment of hyperphosphatemia. [See, by way of example, A J Hutchison and M Wilkie, Clin Kidney J 2012; 5 (Suppl 1): 162-179.] High doses of magnesium salts are required for treatment of hyperphosphatemia, and oral magnesium preparations are frequently poorly tolerated due to their laxative and other gastrointestinal effects. Further, these magnesium salts are insoluble in water. Therefore, although these magnesium salts are effective phosphorus binders and are reported to reduce the risk of vascular calcification, they are unsuitable for use in the present invention.

Administration of pills that are made up of calcium acetate and magnesium carbonate is known to be effective and safe for the treatment of hyperphosphatemia. [See, by way of example, ALM de Francisco, et al., Nephrol Dial Transplant 2010; 25: 3705-3717.] In Europe, a pill called "Osvaren" (Fresenius Medical Care), a combination of calcium acetate and magnesium carbonate and tableting excipients, has been approved for the treatment of hyperphosphatemia of renal disease. Parsons reported successful control of hyperparathyroidism in patients on continuous ambulatory peritoneal dialysis using magnesium carbonate and calcium carbonate as phosphate binders. [Parsons V, et al. Nephron 1993; 63(4): 379-385.] Moreover, animal studies of solid oral dosage forms of calcium acetate and magnesium carbonate have shown that this combination of salts effectively controlled serum phosphate levels in uremic rats and reduced aortic calcification. [De Schutter et al., Kidney Int 2013; 83: 1109-1117.] Further, this same group of investigators found that solid oral dosage forms of calcium acetate and magnesium carbonate reduced vascular calcification without affecting bone in uremic rats. [E Neven, et al., PLoS ONE 9(9): e107067; doi: 10.1371/journal.pone.0107067]. Although the combination of calcium acetate and magnesium carbonate is an effective phosphate binder, the taste of calcium acetate is repugnant and magnesium carbonate is not soluble in water. Thus, this combination is unsuitable for use in the present invention.

Large doses of conventional pills containing calcium acetate and magnesium carbonate are required with each meal for optimal effectiveness, and their side effects—repugnant taste during ingestion, flatulence, and the constipation that often ensues later—produce poor medication compliance. Therefore, phosphorus control may remain suboptimal for patients. Other possible side effects of pills containing calcium acetate and magnesium carbonate include gas, bloating, and headache. Side effects for these compounds are reported to increase in severity with dose. Magnesium carbonate is poorly soluble in slightly acidic or near-neutral solutions, and the fact that gastric acid secretion is often impaired in hyperphosphatemic patients may limit its dissolution and ionization [Gold C H, Morley J E, Viljoen M. et al. Nephron 1980; 25:92-95. Hardy P, Sechet A, Hottelart C. et al. Artif Organs 1988; 22: 569-573. Tan C C, Harden P N, Rodger R S. et al. Nephrol Dial Transplant 1996; 11: 851-853.] Calcium acetate is poorly tolerated, and distaste, "acetic acid breath" ("vinegar breath"), and discomfort have been reported to reduce patient compliance. Increased risk and incidence of hypercalcemia (i.e., serum calcium concentrations in excess of normal values) has been observed in CKD patients using either calcium acetate or calcium carbonate. [Meric F, Yap P, Bia M J. Am J Kidney Dis 1990; 16: 459-464.] Epidemiologic studies show strong independent correlations between risk of death and either hyperphosphatemia, hypercalcemia, or a high calcium-phosphorus product (i.e., [Ca, mg/dL]×[P, mg/dL]). Further, hyperphosphatemic patients frequently suffer from bone deterioration, including osteomalacia and adynamic bone disease. Calcium acetate and calcium carbonate are believed to increase the risk and incidence of bone diseases such as these.

In contrast, a liquid concentrate comprising an aqueous solution comprising calcium propionate and a water-soluble magnesium salt is a palatable, aqueous concentrate useful for phosphorus binding in the gastrointestinal tract. The combination of calcium and magnesium ions is known to bind phosphate with reduced calcium uptake, decreasing the risk of vascular calcification and related cardiovascular events that decrease survival among CKD patients. Thus, the concentrate is expected to match the effectiveness of sevelamer resin (a standard of care) while reducing the risk of calcification associated with conventional calcium-containing phosphorus binding agents. Both the calcium and magnesium ions are already in solution. Thus, patients who use proton-pump inhibitors such as Nexium® or Prilosec® or are achlorhydric can use the concentrate without concerns for poor dissolution of insoluble metal carbonates. Taken together, these attributes are expected to significantly enhance treatment adherence by the CKD patient. Since the volume to be administered can be easily adjusted, the concentrate is a safe and effective phosphorus binding agent for CKD patients of all ages. Therefore, a palatable concentrate of the invention will bring about a radical change in the treatment of hyperphosphatemia. All of these factors are expected to enhance the patient's quality of life.

A unit dose of a liquid concentrate of the present invention comprises a volume of aqueous solution that provides between about 2.5 millimoles (mmol) and 5 mmol calcium as calcium propionate and a second quantity of a magnesium salt equivalent to between 1 mmol and 5 mmol magnesium. The molar ratio of calcium ion to magnesium ion in the concentrate is in the range from 2:1 to 1:2. The magnesium salt is magnesium lactate, magnesium L-lactate, magnesium propionate, magnesium L-theanate, magnesium butyrate, or magnesium threonate. In a preferred embodiment, a unit dose of a liquid composition of the invention comprises 2.7 mmol of calcium as calcium propionate and 2.5 mmol of magnesium as magnesium propionate in 5 milliliters (mL) of water. Each unit dose of the liquid concentrate may also contain 30-60 micrograms of vitamin $K_2$ and 200-400 International Units (IU) of vitamin $D_3$. In a second preferred embodiment, a unit dose of a liquid composition of the invention comprises 2.7 mmol of calcium and 2.5 mmol of magnesium as calcium magnesium propionate in 5 mL of water.

Subjects using the liquid composition will have a broad spectrum of palates. Some subjects may find that the inventive formulation is not sufficiently sweet or has a slightly unpleasant taste. For these subjects, a conventional sweetener, flavor, or taste-masking agent may be added to the liquid concentrate to improve palatability and compliance with dosing regimens. Other subjects may have difficulty swallowing a thin liquid. For these subjects, a conventional thickening agent may be added to the liquid concentrate to improve palatability and compliance with dosing regimens.

In general, the pharmaceutical compositions of this invention can be prepared by conventional techniques, as are described in Remington's Pharmaceutical Sciences, a standard reference in this field [Gennaro A R, Ed. *Remington: The Science and Practice of Pharmacy.* 20th Edition. Baltimore: Lippincott, Williams & Williams, 2000]. For therapeutic purposes, the active components of this invention are ordinarily dissolved in water. The resulting aqueous solution may optionally be combined with one or more excipients to increase patient acceptance. Examples of excipients include those intended to add sweetness, flavors, or mask undesirable taste in certain patient populations, as well as excipients intended to thicken the solution.

The following examples confirm the properties of compositions of the invention. The examples are representative of the scope of the invention, and as such are not to be considered or construed as limiting the invention recited in the appended claims.

Example 1: In Vitro Assessment of Phosphate Binding by a Liquid Composition of the Invention Test Preparations: Solutions of the test article (calcium propionate and magnesium propionate) and control article (calcium acetate) are prepared in deionized, purified water having 18 MO or greater resistance. The pH of each solution is adjusted to the desired value by the addition of concentrated hydrochloric acid or sodium hydroxide, as appropriate.

Tests and Assays: An HPLC method with conductivity detection was developed and validated for use in the determination of propionate, acetate and phosphate. HPLC analysis is performed using a Dionex Aquion ion chromatography system Detection of the anionic species is enabled using a Dionex ED50 Electrochemical Detector, operating in Conductivity Mode. Limits of Detection and Quantitation are enhanced through the use of a Dionex Anion Self-Regenerating Suppressor. After assay-specific development and verification of assay performance is completed, the analysis of phosphate and propionate or acetate is performed by sampling the test solution and diluting it, if necessary, to a concentration within the linear range of the Assay. The sample is then injected onto the HPLC column and eluted with a sodium hydroxide gradient. Data is acquired using Dionex Chromeleon® software.

Experimental Methods: Experiments are performed in triplicate in which 2.77 g of $Na_2HPO_4 \cdot 7H_2O$ (equivalent to 320 mg of elemental phosphorus) is dissolved in 570 mL of deionized water. The test or control binder is dissolved in deionized water to a volume of 30 mL. The binder solution is added to the phosphorus solution to give a final volume of 600 mL. For each binder study, the phosphorus solutions are titrated by addition of dilute HCl or dilute NaOH to five different initial pH levels: 4, 5, 6, 7, and 8. (These solution pH's span the pH range of the gastrointestinal tract after ingestion of food.) Then the beakers containing the solutions are covered and placed on a stir plate that agitates the solution at ~20 cycles per minute overnight. This stirring rate is selected because in vitro antacid activity at such low stirring rates has been reported to correlate well with in vivo antacid activity in the stomach. Samples for ion chromatographic assay of solution phosphate (Pi) are taken at 24 hours post-mixing (the maximum time available for phosphorus binding that has been reported in related in vivo studies). The decrease in phosphorus concentration from the original concentration in the phosphorus solution to that of the filtrate represents the bound phosphorus.

Expected data will demonstrate that Pi binding by calcium acetate, the U.S. standard of care, increases from about 60% at pH 4.5 to over 90% as the pH increases to 6.8. Pi binding by the calcium propionate/magnesium propionate combination is expected to match or exceed the Pi binding activity of calcium acetate at each pH value in the range from pH 4 to 7.

Example 2: Taste Testing

A group of men and women was recruited to taste representative liquid compositions in water. The results of such testing are presented in the table below.

TABLE

Results of taste-testing

| Solution Formulation (per 5 mL) | Initial Taste | Aftertaste |
|---|---|---|
| 2.7 mmol calcium acetate | Repugnantly bitter | Repugnantly bitter |
| 2.7 mmol calcium acetate 2.5 mmol magnesium carbonate | No solution obtained; not tested further | |
| 2.7 mmol calcium acetate 2.5 mmol magnesium lactate | Neutral | Repugnantly bitter |
| 2.7 mmol calcium propionate 2.5 mmol magnesium lactate | Unexpectedly sweet | Slightly spicy |
| 2.7 mmol calcium propionate 2.5 mmol magnesium propionate | Unexpectedly sweet | Unexpectedly sweet |
| 2.7 mmol calcium propionate 2.5 mmol magnesium L-ascorbate | Slightly bitter | Bitter |
| 2.7 mmol calcium propionate 2.5 mmol magnesium L-lactate | Neutral | Slightly spicy |

Notes:
Magnesium L-lactate, known as Puramex® Mg, is available from Corbion (Lenexa, KS).

Example 3. General Procedure to Prepare a Liquid Composition of the Invention

The combination of calcium propionate and magnesium propionate will be used to exemplify the general procedure. In accordance with the formulation, appropriate quantities of calcium propionate and magnesium propionate are accurately weighed and added to the appropriate volume of water. Aliquots of the resulting solution are removed for analysis. If necessary, the solution pH is adjusted into the range 5.5-7.0 by addition of propionic acid. The solution is transferred in defined volumes to glass or plastic containers. The containers are closed and sealed before labeling. The process includes a sterilization step where sterilization is accomplished by aseptic filtration or heating.

| Ingredient | Unit Formulation | Bulk Formulation | Percent (Wt/Vol) |
|---|---|---|---|
| Calcium propionate | 0.505 g | 101 kg | 10.1 |
| Magnesium propionate | 0.510 g | 102 kg | 10.2 |
| Water | 5 mL | 1000 mL | |

Example 4. Efficacy and Safety in Hyperphosphatemic Dialysis Patients

A clinical study is completed in hyperphosphatemic dialysis patients. The study design is similar to that described by Helal et al. [Saudi J Kidney Dis Transpl 2016; 27(6): 1162-1167] After an initial 2-week washout period, serum phosphorus (sPho), serum calcium (sCa), and serum magnesium (sMg) will be determined in 35 hyperphosphatemic dialysis patients. Sixteen patients who have sPho≥1.8 mmol/L, sCa≤2.6 mmol/L, and sMg≤1.5 mmol/L will be treated with a calcium/magnesium-containing liquid concentrate of the invention. The dose will be titrated initially and at weeks 4, 6, 8, 10, and 12, according to sPho levels exhibited by the subject:

5 mL of concentrate×3/day if sPho is between 1.8 and 2.2 mmol/L;
  10 mL of concentrate×3/day if sPho is between 2.3 and 2.7 mmol/L; and
  15 mL of concentrate×3/day is sPho is >=2.8 mmol/L.

The initial dose will be increased or decreased depending on the levels of sPho, sCa, and sMg at weeks 4, 6, 8, 10, and 12.

After 12 weeks of treatment, the following results are expected.

Serum phosphorus will exhibit a steady and significant decrease.
  Serum calcium will fluctuate but will not change significantly.
  Serum magnesium will fluctuate and may increase to high normal concentrations (i.e., to serum magnesium concentrations of 1.1-1.2 mmol/L).
  Patients will tolerate the treatment well. No unexpected adverse effects will be observed.
  The serum triglyceride levels in some patients will decrease, indicating gluconeogenesis and an absence of ketosis.

After cessation of treatment, the patient's serum phosphate concentration will rise.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

I claim:

1. A method for binding phosphorus within the gastrointestinal tract of a subject in need there of, comprising orally administering to said subject a liquid concentrate comprising:
    an aqueous solution of calcium propionate and a magnesium salt in a molar ratio of from 1.5:1 to 1:1.5, wherein the calcium propionate concentration in said aqueous solution is from 0.175 to 0.375 molar, the magnesium salt concentration in said aqueous solution is from 0.15 to 0.35 molar, the pH of said aqueous solution is in the range from pH 5 to pH 7.5, and said magnesium salt is selected from the group consisting of magnesium lactate, magnesium L-lactate, magnesium propionate, magnesium threonate, magnesium butyrate, and magnesium theanate.

2. The method of claim 1, wherein the molar ratio of calcium propionate:magnesium salt is from 1.3:1 to 1:1.3.

3. The method of claim 1, wherein the molar ratio of calcium propionate:magnesium salt is about 1.1:1.

4. The method according to claim 1, wherein said aqueous solution contains about 24 milligrams calcium and 12 milligrams magnesium per milliliter of said aqueous solution.

5. The method according to claim 1, wherein said aqueous solution contains 6-10 micrograms of vitamin $K_2$ and 40-80 International Units of vitamin $D_3$ per milliliter of said aqueous solution.

6. A method for providing calcium and magnesium as an oral liquid to a subject in need thereof, comprising dissolving calcium propionate and magnesium propionate in water to provide an aqueous solution wherein the calcium propionate concentration in said aqueous solution is from 0.175 to 0.375 molar and the magnesium propionate concentration in said aqueous solution is from 0.15 to 0.35 molar, the molar ratio of calcium propionate:magnesium propionate of from 1.5:1 to 1:1.5, and adjusting the pH of the resulting concentrate into the range from pH 5 to pH 7.5.

7. The method according to claim 6, further comprising adding about 6-10 micrograms of vitamin $K_2$ and 40-80 International Units of vitamin $D_3$ per milliliter to said aqueous solution.

8. An oral aqueous solution effective at treating a subject in need thereof comprising calcium magnesium propionate, wherein the calcium magnesium propionate concentration in the said solution is from 0.175 to 0.375 molar, the pH of said solution is from pH 5 to pH 7.5, and the molar ratio of calcium to magnesium in said salt is in a range from 1:2 to 2:1.

9. The aqueous solution of claim 8, wherein the molar ratio of calcium:magnesium in said salt is from 1.3:1 to 1:1.3.

10. The aqueous solution of claim 8, wherein the molar ratio of calcium propionate:magnesium salt is about 1.1:1.

11. The aqueous solution of claim 8, wherein said aqueous solution contains about 24 milligrams calcium and 12 milligrams magnesium per milliliter of said aqueous solution.

12. The aqueous solution of claim 8, wherein said aqueous solution contains 6-10 micrograms of vitamin $K_2$ and 40-80 International Units of vitamin $D_3$ per milliliter of said aqueous solution.

13. A method for reducing the pill burden of a hyperphosphatemic subject, comprising orally administering to said subject a liquid concentrate comprising an aqueous solution of from about 1.5 to 3.5 mmol calcium magnesium propionate in each 5 mL of said aqueous solution, said aqueous solution having a pH of from 5 to 7.5, wherein the method is effective at treating hyperphosphatemia.

14. The method according to claim 13, wherein said aqueous solution contains about 20 to 50 milligrams calcium and 10 to 25 milligrams magnesium per milliliter of said aqueous solution.

15. The method according to claim 13, wherein said aqueous solution contains 6-10 micrograms of vitamin $K_2$ and 40-80 International Units of vitamin $D_3$ per milliliter of said aqueous solution.

16. A method for providing to a subject in need thereof calcium and magnesium as an oral liquid concentrate, comprising dissolving calcium magnesium propionate in water to provide an aqueous solution comprising from 0.15 to 0.35 molar calcium magnesium propionate and adjusting the pH of the resulting concentrate into the range from pH 5 to pH 7.5.

17. The method according to claim 16, further comprising adding about 6-10 micrograms of vitamin $K_2$ and 40-80 International Units of vitamin $D_3$ per milliliter to said aqueous solution.

18. An oral aqueous solution effective at treating a subject in need thereof comprising 1.5 to 3.5 mmol calcium magnesium propionate in each 5 mL of said aqueous solution, said aqueous solution having a pH of from 5 to 7.5.

19. The aqueous solution according to claim 18, wherein said aqueous solution contains about 20 to 50 milligrams calcium and 10 to 25 milligrams magnesium per milliliter of said aqueous solution.

20. The aqueous solution according to claim 18, wherein said aqueous solution contains 6-10 micrograms of vitamin $K_2$ and 40-80 International Units of vitamin $D_3$ per milliliter of said aqueous solution.

* * * * *

UNITED STATES PATENT AND TRADEMARK OFFICE
CERTIFICATE OF CORRECTION

Page 1 of 1

PATENT NO. : 12,251,400 B2
APPLICATION NO. : 17/603072
DATED : March 18, 2025
INVENTOR(S) : Deanna J. Nelson It is certified that error appears in the above-identified patent and that said Letters Patent is hereby corrected as shown below:

In the Claims

Claim 6, Column 12, Line 16 reads:
"oral liquid to a subject in need thereof, comprising dissolv-".
Whereas it should read:
"oral liquid concentrate to a subject in need thereof, comprising dissolv-".

Signed and Sealed this
Third Day of June, 2025

Coke Morgan Stewart
*Acting Director of the United States Patent and Trademark Office*